(12) United States Patent
Cheng

(10) Patent No.: US 6,280,996 B1
(45) Date of Patent: Aug. 28, 2001

(54) METHOD OF USING OXYGEN TO ELIMINATE CARBON DIOXIDE POISONING IN AEROBIC FERMENTATION

(75) Inventor: Alan Tat Yan Cheng, Livingston, NJ (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 09/273,980

(22) Filed: Mar. 22, 1999

(51) Int. Cl.$^7$ .............................. C12N 1/00; C12M 1/36
(52) U.S. Cl. ........................ 435/243; 435/286.6
(58) Field of Search ................... 435/286.6, 243

(56) References Cited

U.S. PATENT DOCUMENTS

| | | | |
|---|---|---|---|
| 3,847,748 | 11/1974 | Gibson et al. | 195/109 |
| 4,001,090 | 1/1977 | Kalina | 195/109 |
| 4,041,180 | * 8/1977 | Wilson | 426/11 |
| 4,444,882 | 4/1984 | Shimizu et al. | 435/29 |
| 4,670,397 | 6/1987 | Wegner et al. | 435/289 |
| 4,782,024 | 11/1988 | Scott et al. | 435/247 |
| 4,846,965 | 7/1989 | Clifft et al. | 210/96.1 |
| 4,959,322 | 9/1990 | Mari | 435/311 |
| 5,356,600 | 10/1994 | Kiyonaga et al. | 422/234 |

FOREIGN PATENT DOCUMENTS

| | | |
|---|---|---|
| 4235558 | 5/1994 | (DE) . |
| 7618650 | 2/1977 | (FR) . |
| 2317169 | 3/1998 | (GB) . |

OTHER PUBLICATIONS

Yabannavar et al. Journal of Fermentation and Bioengineering. 1992. vol. 73, No. 1, pp. 66–69.*
Han et al. Biotechnology Progress. 1992. vol. 8, No. 1, pp. 5–10.*
Cysewsky et al., "Rapid Ethanol Fermentation Using Vacuum and Cell Recycle" Biotechnology and Bioengineering. Including: Symposium Biotechnology In Energy Production and Conservation. vol 19, No. 8, 1977, pp. 1125–1143.

* cited by examiner

Primary Examiner—Sandra E. Saucier
Assistant Examiner—Vera Afremova
(74) Attorney, Agent, or Firm—Bernard Lau

(57) ABSTRACT

A method for carrying out fermentation comprising the steps of providing a vessel with elevated pressure up to 25 atm which contains a broth comprising a constituent capable of undergoing fermentation, lowering the vessel pressure within the vessel to lower the equilibrium oxygen partial pressure, adding pure oxygen into the vessel to raise the equilibrium oxygen partial pressure therein, and utilizing the pure oxygen to carry out the fermentation of the constituent.

14 Claims, No Drawings

METHOD OF USING OXYGEN TO ELIMINATE CARBON DIOXIDE POISONING IN AEROBIC FERMENTATION

TECHNICAL FIELD

This invention relates generally to a fermentation method and, more particularly, to fermentation method which is driven by an injected gas such as oxygen.

BACKGROUND ART

Fermentation is a chemical change induced by a living organism or enzyme, such as bacteria or the microorganisms occurring in unicellular plants, which involves the aerobic decomposition of hydrocarbons to produce a desired product along with carbon dioxide. Fermentation systems are used for the production of a large number of products such as antibiotics, vaccines, synthetic biopolymers, synthetic amino acids and edible proteins.

In conventional aerobic fermentation, air is supplied in large quantity to provide oxygen for respiration and growth. At the same time, carbon dioxide is stripped off by the remaining air that is not consumed by the biomass (bacteria, fungi, plant cells, etc.). Generally, the oxygen contained in the air bubbles must be dissolved in the broth before the biomass can consume it. Therefore, oxygen dissolution from air is a rate controlling factor. To maintain favorable air dissolution rate, the pressure of the fermenters are typically elevated to several atmospheres.

Increased productivity in a fermenter may involve increasing the concentration of the nutrient and biomass. Oxygen demand will accordingly increase in response to the additional nutrient and biomass concentration. More oxygen will be consumed if it is available. Therefore, supplying sufficient air (or oxygen) to the biomass is a major concern. At higher oxygen consumption rate, more carbon dioxide is produced. At some point, the level of carbon dioxide in the fermenter will poison the biomass and become a major problem in the fermentation process. This poisoning occurs when the amount of carbon dioxide being generated during respiration and growth of the biomass is faster than the removal rate. At a critical level, the excess dissolved carbon dioxide will retard the growth of the biomass. The critical carbon dioxide level is defined as the level of carbon dioxide in the fermentation vessel in which the carbon dioxide no longer serves a beneficial function in fermentation, but rather retards the growth of the biomass.

Since the carbon dioxide concentration in the exhaust of the fermenter is a much easier measurable value than dissolved carbon dioxide level within the fermenter, it has become an industrial standard to measure the carbon dioxide concentration in the exhaust. Therefore, each fermentation process has a certain predetermined critical carbon dioxide concentrate in the exhaust as a reference that the fermentation batches should not exceed. This critical carbon dioxide concentration in the exhaust has become a practical measurable limitation as one tries to increase the productivity or biomass concentration.

To increase productivity with higher biomass, it has been known in the art to increase the air flow. Increasing the air flow has the advantages of supplying extra oxygen to support denser biomass while stripping out more carbon dioxide. However, there is a practical limit as to the amount of air that can be introduced. Excess air will flood the impeller if the fermenter is mechanically agitated, thus rendering the agitator useless. In airlifted fermenters, it can also fluidize the broth or blow the content out of the fermenters. Therefore, an increase in air flow can only increase the productivity to a very small extent.

Other works have suggested the use of pure oxygen to supplement the air when the biomass concentration is high. However, it is believed that simply adding pure oxygen will work in fermentation only if the biomass is resistant to carbon dioxide poisoning. To the most part, the addition of pure oxygen will compound the problem since more carbon dioxide is being generated through respiration and growth of the biomass. Excess carbon dioxide will accumulate if the removal rate is not increased at a rate higher than the carbon dioxide production.

It has been known in the art to keep the biomass concentration low enough so that the carbon dioxide concentration in the exhaust (as a control method) will not exceed the critical value. Therefore, the carbon dioxide concentration in the exhaust is a limiting factor in productivity increase.

The art has only proposed solutions relating to increase oxygen dissolution rate while ignoring the effect of carbon dioxide poisoning. The prior art references provided for using oxygen in enrichment or direct injection, but none of them is believed to resolve the problems associated with carbon dioxide poisoning.

It is desirable, therefore, to provide a method for carrying out fermentation using oxygen which minimizes the effects of carbon dioxide poisoning.

SUMMARY OF THE INVENTION

This invention is directed to a method for carrying out fermentation. The method steps involve providing a vessel which contains a broth comprising a constituent capable of undergoing fermentation, lowering the vessel pressure within the vessel to lower the dissolved carbon dioxide level and the equilibrium oxygen partial pressure in the vessel proportional to the lowered vessel pressure, adding pure oxygen into the vessel to raise the equilibrium oxygen partial pressure therein, and utilizing the pure oxygen to carry out the fermentation of the constituent. Preferably, this invention provides for the simultaneous steps of lowering the reactor pressure and adding pure oxygen. This invention is also directed to a method for increasing the biomass concentration in carrying out the fermentation process.

DETAILED DESCRIPTION OF THE INVENTION

This invention is based on the premise that most processors control the carbon dioxide level in the exhaust of the fermentation vessel. On that basis, the exhaust carbon dioxide level is proportional to the dissolved carbon dioxide level. Notwithstanding this premise, it is believed that the exhaust carbon dioxide level is not always proportional, but rather dependent on the temperature and pressure of the fermenter.

The reason that the carbon dioxide concentration in the gas exhaust is used for measuring the rate of fermentation and the productivity of fermentation instead of the dissolved carbon dioxide is because the dissolved carbon dioxide level in a sterile reacting broth is not a measurable value as there is not believed to be any presently existing on-line equipment capable of calculating such a value. This invention uses the critical carbon dioxide measured from the exhaust of the fermentation vessel to calculate the critical dissolved carbon dioxide level. By reducing the pressure inside a fermenter, the actual dissolved carbon dioxide level, $X_{CO2}$, will decrease proportionally due to an reduction in carbon dioxide partial pressure:

$$P_{CO2}=y_{CO2}.P=H.X_{CO2}$$

where $P_{CO2}$=Partial pressure of $CO_2$ $Y_{CO2}$=Mole fraction of $CO_2$ in the gas phase $X_{CO2}$=Mole fraction of dissolved $CO_2$ in the liquid phase H=Henry Law's constant Therefore, a higher biomass with pure oxygen can be added to boost production. With higher growth and respiration rate, the carbon dioxide level in the exhaust will appear to be higher than the critical carbon dioxide level in the exhaust. However, the dissolved carbon dioxide level remains the same or slightly lower.

The reduction in fermenter pressure will proportionally reduce the dissolved oxygen level due the reduction of oxygen partial pressure:

$$P_{CO2}=Y_{O2}.P=H.X_{O2}$$

where $P_{CO2}$=Partial pressure of $CO_2$ $Y_{O2}$=Mole fraction of $O_2$ in the gas phase $X_{O2}$=Mole fraction of dissolved $O_2$ in the liquid phase H=Henry Law's constant To compensate for the reduction in equilibrium oxygen partial pressure, additional pure oxygen is used in this invention through simple oxygen enrichment or direct oxygen injection. Subsequently, higher productivity can be achieved with the same critical dissolved carbon dioxide level but with a higher oxygen consumption rate.

Reducing the fermenter pressure has the opposite effects of adding pure oxygen. Based on the art, the skilled artisan would not ordinarily employ both techniques to reduce the fermenter pressure and to add pure oxygen. However, contrary to the art, this invention discovered that the degree of influence is different between the two techniques. By using both techniques, one can still dissolved additional oxygen while gaining the benefit of lower dissolved carbon dioxide level in the broth.

In fact, this invention provides a break through for increasing fermenter productivity beyond the limit posted by the critical carbon dioxide concentration in the exhaust. This is achieved through simultaneous reduction in fermenter pressure and addition of pure oxygen.

To increase the oxygen dissolution rate, fermenters are usually operated at elevated pressure of several atmospheres. Increasing the absolute pressure by a factor of two will be expected to increase the amount of dissolved oxygen also by a factor of two at equilibrium. However, this invention realizes that operating at higher pressure also reduce the ability of the fermenter to remove carbon dioxide. This is because the solubility of carbon dioxide is also increased at higher pressure. Most fermentation broth are sensitive to carbon dioxide poisoning so that the dissolved carbon dioxide must be maintained below a critical level. Since the level of dissolved carbon dioxide is very difficult to measure, the industry can only monitor the carbon dioxide gas concentration in the exhaust.

Because of the production limit based on the critical carbon dioxide level, it is generally not possible to increase the productivity (pounds of product per given volume of fermentation broth) at higher biomass level. Higher biomass will generate more carbon dioxide and will also require more oxygen in the fermentation process. Conventional approach to maintain the carbon dioxide gas concentration and to increase oxygen supply is to add more air. However, it is usually impractical or impossible to increase air flow for an optimized fermenter. The excess air can flood the impellers with gas, causing the impeller to malfunction. Most plants are already running air compressors to the maximum and the existing line size and sparge ring opening will also limit the amount of air can supply.

The present invention uses direct oxygen injection (or enrichment) while operating the fermenter at a lower pressure. By cutting the absolute pressure in half (e.g., from 4 atm to 2 atm, or 3 atm-gauge to 1 atm-gauge), it reduces the equilibrium oxygen concentration in half. However, the reduction in equilibrium oxygen concentration can be compensated by using pure oxygen, which has a driving force of about five times higher than the equilibrium oxygen concentration. Therefore, the pure oxygen will compensate the effect of pressure reduction and also increase the oxygen availability.

EXAMPLE

Control Parameters

Pressure=4 atm $CO_2$ measured in exhaust=$y_1$=5%

$$\text{Dissolved } CO_2 \text{ (critical, not measured)}=X_{1,CO2}=Y_{1,CO2}\, P_1/H \quad (1)$$

where $y_{1,CO2}$=Critical gas phase carbon dioxide concentration (measured)

$P_1$=Pressure of the fermenter

H=Henry's law constant

Oxygen consumption=50 mmole/liter-hr

Available oxygen from air=0.21*100 $Nm^3$/hr=21 $Nm^3$/hr

Oxygen Case with Higher Productivity

In this case, pure oxygen is added to supplement the air. The fermenter pressure is reduced at the same time.

Biomass concentration=2×control

Pressure=2 atm

By doubling the biomass concentration, the oxygen consumption is also doubled.

Oxygen consumption=2×control=2*50=100 mmoles/liter-hr

At the same time, carbon dioxide generation is also doubled.

$CO_2$ generated=2×control

The additional oxygen requirement is then satisfied by using pure oxygen:

Available oxygen

=oxygen from air+pure oxygen

=0.21*100 $nM^3$/hr+21 $Nm^3$/hr (pure oxygen)

=42 $Nm^3$/hr

In this invention, it is believed that the critical dissolved carbon dioxide is the primary factor which is actually effecting the biomass activity, not the gas phase carbon dioxide concentration.

Therefore, it is necessary to keep the dissolved carbon dioxide unchanged.

$$\text{Dissolved } CO_2 \text{ (critical, not measured)=same as control}=X_{1,CO2}=X_{2,CO2}=_{Y2,CO2}\, P_2/H=Y_{2,CO2}\,(P_1/2)/H \quad (2)$$

In contrast to the process in the present state of the art, the maximum allowable gas phase carbon dioxide concentration measured in exhaust can actually be different. The new maximum carbon dioxide concentration allowed in exhaust (calculated)=$Y_{2,CO2}$=$Y_{1,CO2}$*2=10%

Therefore, the maximum allowable carbon dioxide concentration in the exhaust with 2 atm should be twice as high as the one operating at 4 atm. The actual carbon dioxide concentration measured in exhaust with doubled bio activity=5% *2* (100/(100+21))=8.26%

As can be seen from above, the actual carbon dioxide concentration measured in the exhaust of 8.26% is less than the 10% new maximum allowable carbon dioxide concentration limit in the exhaust. Therefore, the concentration of the oxygen supplied can be twice the concentration of the biomass (two times as concentrated), and still not increase the carbon dioxide concentration beyond the critical level.

Accordingly, the biomass concentration can be increased beyond what is normally considered to be a limitation caused by the carbon dioxide concentration in the exhaust. This is accomplished by reducing the fermenter pressure while compensating for the drop in oxygen dissolution with pure oxygen. Note that this invention also contemplates adding credits to the economical benefits of the fermentation process because the compressor power can be cut by at least 50%.

To take advantage of high oxygen dissolution and fast carbon dioxide removal, it is preferable to operate the fermenter with a pressure of less than 2 atmospheres while injection pure oxygen. The vacuum on the fermenter can be pulled if necessary. Generally, the vessel pressure of this invention can be lowered from up to about 25 atmospheres to any pressure between about 25 atmospheres and about 1 atmosphere. The pressure may be any pressure within this range. For example, the vessel pressure may be lowered to any pressure between about 25 atmospheres to about 1 atmosphere.

Fermentation products which can be produced by the method of this invention include antibiotics such as penicillin, erythromycin and tetracycline, organic chemicals such as sorbitol and citronellol, organic acids such as citric acid, tartaric acid and lactic acid, amino acids such as L-lysine and monosodium glutamate, polysaccharides such s baker's yeast and xanthan gum, vitamins such as ascorbic acid and riboflavin, and other products including enzymes, insecticides, alkaloids, hormones, pigments, steroids, vaccines, interferon and insulin.

The same principle may be applied to organic oxidation with air. This can be oxidation of any organic when the gas phase products or byproducts may inhibit the reaction. The inhibition can be due to equilibrium shift or poisoning of the catalyst sites. Reducing the reactor pressure will decrease the equilibrium dissolved level of gaseous products or byproducts. The reduction in oxygen dissolution rate is then compensated by adding pure oxygen.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for carrying out fermentation comprising:
   a. providing a vessel with a pressure up to 25 atmospheres which contains a broth comprising a constituent capable of undergoing fermentation and a biomass capable of fermenting the constituent;
   b. lowering the vessel pressure within said vessel to lower the equilibrium oxygen partial pressure and the dissolved carbon dioxide concentration in the vessel proportional to said lowered vessel pressure wherein said vessel pressure is lowered between 25 atmospheres and about 1 atmosphere;
   c. adding pure oxygen into said vessel to raise said equilibrium oxygen partial pressure therein; and
   d. utilizing said pure oxygen to carry out the fermentation of said constituent.

2. The method of claim 1 wherein said lowering the vessel pressure and adding pure oxygen take place simultaneously.

3. The method of claim 1 wherein lowering said vessel pressure results in lowering the dissolved oxygen concentration and dissolved carbon dioxide concentration in said vessel.

4. The method of claim 1 wherein adding said pure oxygen into said vessel raises the level of said equilibrium oxygen partial pressure greater than 0.21 atmosphere.

5. The method of claim 1 wherein said adding of pure oxygen is by simple oxygen enrichment or direct oxygen injection.

6. A method for increasing the biomass concentration in carrying out fermentation comprising:
   a. providing a vessel with a pressure up to 25 atmospheres which contains a broth comprising a constituent capable of undergoing fermentation and a biomass capable of fermenting the constituent;
   b. lowering the vessel pressure within said vessel to lower the equilibrium oxygen partial pressure and the dissolved carbon dioxide concentration in the vessel proportional to said lowered vessel pressure wherein said vessel pressure is lowered between 25 atmospheres and about 1 atmosphere;
   c. adding pure oxygen into said vessel to raise said equilibrium oxygen partial pressure therein; and
   d. utilizing said pure oxygen to carry out the fermentation of said constituent.

7. The method of claim 6 wherein said lowering the vessel pressure and adding pure oxygen take place simultaneously.

8. The method of claim 6 wherein lowering said vessel pressure results in lowering the dissolved oxygen concentration and dissolved carbon dioxide concentration in said vessel.

9. The method of claim 6 wherein adding said pure oxygen into said vessel raises the level of said equilibrium partial oxygen pressure greater than 0.21 atmosphere.

10. The method of claim 6 wherein said adding of pure oxygen is by simple oxygen enrichment or direct oxygen injection.

11. The method of claim 1 further comprising allowing the dissolved carbon dioxide concentration to be the same or lower than in step a, while the carbon dioxide concentration in the exhaust is higher than the critical carbon dioxide concentration of the exhaust previously determined under the conditions of step a and below the new critical carbon dioxide exhaust concentration.

12. The method of claim 6 further comprising allowing the dissolved carbon dioxide concentration to be the same or lower than in step a, while the carbon dioxide concentration in the exhaust is higher than the critical carbon dioxide concentration of the exhaust previously determined under the conditions of step a and below the new critical carbon dioxide exhaust concentration.

13. The method of claim 1 comprising lowering the vessel pressure by pulling a vacuum on said vessel.

14. The method of claim 6 comprising lowering the vessel pressure by pulling a vacuum on said vessel.

* * * * *